United States Patent
Oota

(10) Patent No.: US 7,172,340 B2
(45) Date of Patent: Feb. 6, 2007

(54) X-RAY IMAGING APPARATUS AND METHOD FOR MOVING X-RAY DETECTOR

(75) Inventor: Satoshi Oota, Imaichi (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 6 days.

(21) Appl. No.: 10/958,391

(22) Filed: Oct. 6, 2004

(65) Prior Publication Data

US 2005/0117703 A1 Jun. 2, 2005

(30) Foreign Application Priority Data

Oct. 8, 2003 (JP) ............................ 2003-349433

(51) Int. Cl.
- *H05G 1/26* (2006.01)
- *H05G 1/64* (2006.01)
- *G01R 27/26* (2006.01)

(52) U.S. Cl. .................... 378/189; 378/91; 378/98.8; 324/662

(58) Field of Classification Search ............... 378/117, 378/189, 196, 197, 198, 91, 98.8; 324/658, 324/661, 662, 663
See application file for complete search history.

(56) References Cited

U.S. PATENT DOCUMENTS

| | | | |
|---|---|---|---|
| 4,188,537 A * | 2/1980 | Franke | 378/39 |
| 4,979,197 A * | 12/1990 | Troxler et al. | 378/90 |
| 5,097,493 A * | 3/1992 | Hillen et al. | 378/98.2 |
| 5,651,044 A * | 7/1997 | Klotz et al. | 378/117 |
| 5,805,658 A * | 9/1998 | Hum et al. | 378/4 |
| 5,805,664 A * | 9/1998 | Whipple et al. | 378/117 |
| 5,828,221 A * | 10/1998 | Habraken et al. | 324/662 |
| 5,883,935 A * | 3/1999 | Habraken et al. | 378/117 |
| 5,912,943 A * | 6/1999 | Deucher et al. | 378/98.8 |
| 6,408,051 B2 * | 6/2002 | Habraken et al. | 378/117 |
| 6,548,796 B1 * | 4/2003 | Silvermintz et al. | 250/201.3 |
| 6,661,240 B1 * | 12/2003 | Johnson et al. | 324/662 |
| 6,700,392 B2 * | 3/2004 | Haase | 324/674 |
| 6,985,556 B2 * | 1/2006 | Shanmugavel et al. | 378/117 |
| 2006/0097734 A1 * | 5/2006 | Roziere | 324/662 |

FOREIGN PATENT DOCUMENTS

| | | |
|---|---|---|
| JP | 2001-208504 | 8/2001 |
| JP | 2001-241910 | 9/2001 |
| JP | 2001-336908 | 12/2001 |

* cited by examiner

*Primary Examiner*—Allen C. Ho
(74) *Attorney, Agent, or Firm*—Oblon, Spivak, McClelland, Maier & Neustadt, P.C.

(57) ABSTRACT

An X-ray imaging apparatus includes an X-ray irradiating unit configured to irradiate an X-ray to an object, an X-ray detecting unit configured to detect the irradiated X-ray, an image creating unit configured to create X-ray image data based on data detected by the X-ray detecting unit, a moving mechanism configured to move the X-ray detecting unit to the object, a capacitance sensing unit, including an electrode which is positioned so as to cover at least part of a detection plane of the X-ray detecting unit, configured to obtain a capacitance value of the X-ray detecting unit by the electrode and a distance measurement unit configured to measure a distance between the object and the X-ray detecting unit based on the capacitance value.

18 Claims, 8 Drawing Sheets

X-RAY IMAGING APPARATUS AND METHOD FOR MOVING X-RAY DETECTOR

CROSS-REFERENCE TO RELATED APPLICATIONS

This application is based upon and claims the benefit of priority from prior Japanese Patent Application No. 2003-349433 filed on Oct. 8, 2003, the entire contents of which are incorporated herein by reference.

FIELD OF THE INVENTION

The present invention relates generally to an X-ray imaging apparatus and a method for moving X-ray detector.

BACKGROUND

Generally, an angio X-ray imaging apparatus includes an X-ray generating part, an X-ray detecting part, a supporting part which supports the X-ray generating part and the X-ray detecting part, a bed and a processor, for example. The supporting part is a C-arm or an Ω-arm, for example, and the supporting part moves such that images of a patient are obtained from several angles or positions.

As a detector of the detecting part, an X-ray film or an I.I. (Image Intensifier) is used, for example. In an imaging of the I.I., an X-ray tube of the X-ray generating part irradiates an X-ray to the patient, and the I.I. transfers the X-ray penetrated through the patient into an optical image. The optical image is changed to electric signals by an X-ray TV camera. The electric signals are converted by A/D converter and are displayed on a monitor as an X-ray image. In an imaging of the film, it is impossible to display the X-ray image in real time, however in the imaging of the I.I., a real time imaging can be performed. In addition, digital signals are obtained, several image processes can be performed. Recently, in stead of the I.I., a X-ray flat panel detector (referred to as a flat panel detector below) which has detection elements arranged in two dimension is developed.

It is required that an imaging part including the X-ray generating part and the X-ray detecting part speedily moves in a wide range in order to move the C-arm according to a flow of a contrast agent in a blood vessel.

In this case, in order to obtain clear image data, it is required to arrange the flat panel detector in a predetermined position close to a surface of a body of the patient surface, and when the flat panel detector contacts the body of the patient, a movement of the X-ray detecting part stops by using a contact type sensor as one method.

However, in this method, it is difficult to stop the X-ray detecting part quickly, and the patient may be contacted-to the X-ray detecting part.

Therefore, non-contact type capacitance sensor is used, recently.

In this method, the capacitance sensor is attached around the flat panel detector of the X-ray detecting part. Using information of the capacitance which changes according to a position of the patient, a distance of the patient's body surface and the flat panel detector is measured. Based on information of the measured distance, speed of the movement of the X-ray detecting part is slowed down gradually, and the X-ray detecting part stops at a predetermined position near the patient. In this method, it is possible to move the X-ray detecting part at high speed to a position close to the patient's body surface, and efficiency for diagnosis improves. And it is possible to obtain an image even if the flow of the blood is fast.

However, In the method using an above-mentioned capacitance sensor, even if the distance between the flat panel detector and the patient's body surface is constant, a value of the measured capacitance changes according to a shape, sex, age, degree of obesity, etc. of the patient. For this reason, it is difficult to stop the flat panel detector at a desired position, since the distance between the flat panel detector to be stopped and the patient body surface is different by each patient.

Regarding the problem caused by the above-mentioned patient's shape, first, by presuming the patient's surface based on change of the value of the capacitance according to the movement of the X-ray detecting part. Thereafter, the value of the capacitance to be measured is corrected based on the presumed patient's surface. Thereby, X-ray detecting part can be positioned at a desired position. The technique is disclosed in Japanese Patent Publication (Kokai) No. 2001-241910 (pp 4-7 and FIG. 1 to 9).

In this method, it is possible to set the X-ray detecting part at a appropriate position automatically by correcting the value of the capacitance measured even if the shape of the patient's body surface differs. However, since this method is complex, it is difficult to correct the value of the capacitance, constantly. Or, since the capacitance sensor is attached around the X-ray detecting part, an electromagnetic field formed is not be uniformed to the patient's body surface. When the surface of the patient is an odd-shaped, it is difficult to measure the distance between the patient and the X-ray detecting part correctly.

Further, in this method, it is also difficult to correct the value of the capacitance caused by error factors other than the patient's shape, the X-ray detecting part does not stop at a desired position.

SUMMARY

One object of the present invention is to ameliorate at least one problem described above.

According to one aspect of the present invention, there is provided an X-ray imaging apparatus includes an X-ray irradiating unit configured to irradiate an X-ray to an object, an X-ray detecting unit configured to detect the irradiated X-ray, an image creating unit configured to create X-ray image data based on data detected by the X-ray detecting unit, a moving mechanism configured to move the X-ray detecting unit to the object, a capacitance sensing unit, including an electrode which is positioned so as to cover at least part of a detection plane of the X-ray detecting unit, configured to obtain a capacitance value of the X-ray detecting unit by the electrode and a distance measurement unit configured to measure a distance between the object and the X-ray detecting unit based on the capacitance value.

According to another aspect of the present invention, there is provided an X-ray imaging apparatus includes an X-ray irradiating unit configured to irradiate an X-ray to an object, an X-ray detecting unit configured to detect the irradiated X-ray, an image creating unit configured to create X-ray image data based on data detected by the X-ray detecting unit, a moving mechanism configured to move the X-ray detecting unit to the object, a capacitance sensing unit configured to obtain a capacitance value of the X-ray detecting unit by the electrode, an environment sensing unit configured to obtain environment information around the object, a capacitance correction unit configured to correct the capacitance value based on the environment information and a distance measurement unit configured to measure a distance between the object and the X-ray detecting unit based on the corrected capacitance value.

According to another aspect of the present invention, there is provided an X-ray imaging apparatus includes an X-ray irradiating unit configured to irradiate an X-ray to an object, an X-ray detecting unit configured to detect the irradiated X-ray, an image creating unit configured to create X-ray image data based on data detected by the X-ray detecting unit, a moving mechanism configured to move the X-ray detecting unit to the object, a capacitance sensing unit configured to obtain a capacitance value of the X-ray detecting unit by the electrode, an input device configured to input information of the object, a capacitance correction unit configured to correct the capacitance value based on the object information and a distance measurement unit configured to measure a distance between the object and the X-ray detecting unit based on the corrected capacitance value.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF EXEMPLARY EMBODIMENTS

Hereafter, with reference to drawings, an embodiment is explained below.

In this embodiment, a capacitance sensor is a sheet shaped, and the capacitance sensor covers an X-ray detection plane of the flat panel detector.

Furthermore, in this embodiment, when the distance between the X-ray detection plane and the patient's body surface is presumed, a predetermined correction value corresponding to the patient's shape, age, sex and degree of obesity is applied to the value of the capacitance which is previously measured, and the presumption of the distance is performed based on the corrected value of the capacitance.

Figure 1:
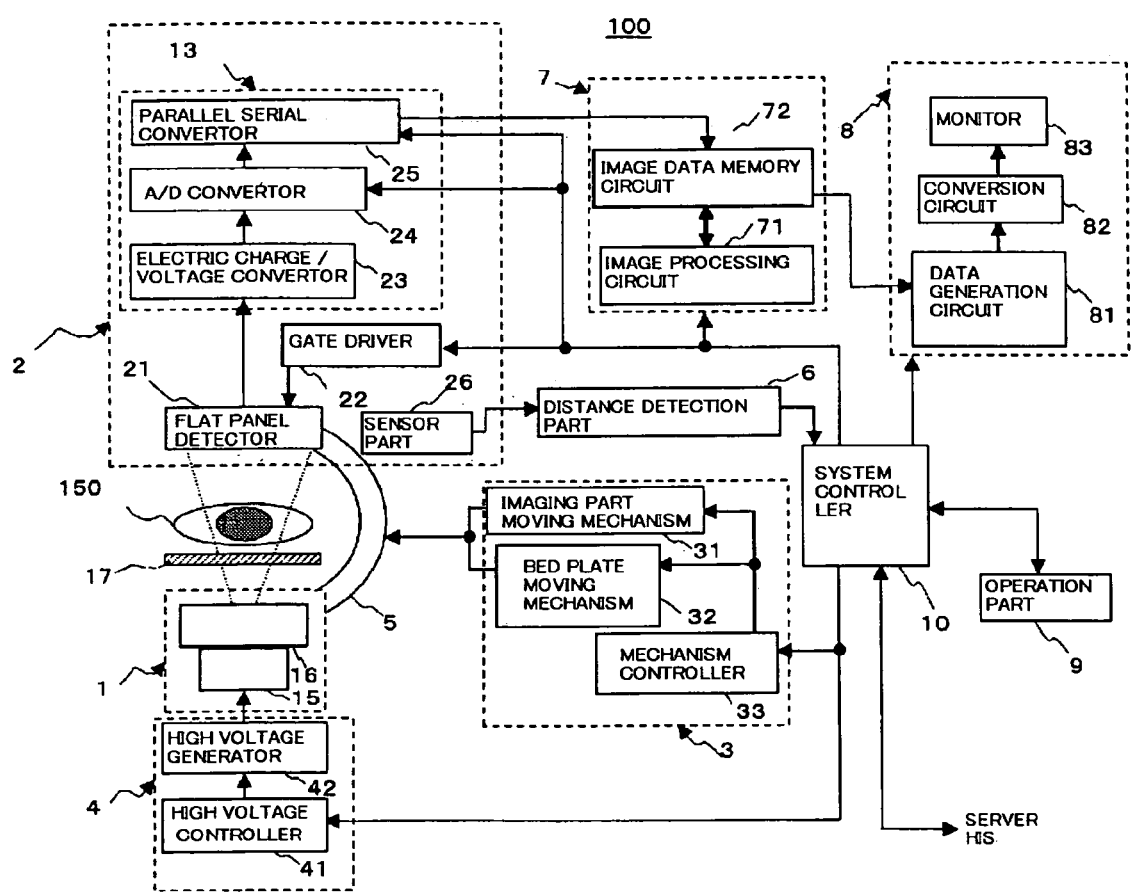
FIG. 1 is block diagram of an X-ray imaging apparatus according to an embodiment.

An X-ray imaging apparatus is explained, referring to FIG. 1 through FIG. 5. FIG. 1 shows a block diagram of the X-ray imaging apparatus.

The X-ray imaging apparatus 100 shown in FIG. 1 includes an X-ray generating part 1 which irradiates an X-ray to a patient 150, a high voltage generating part 4 which generates a high voltage supplied to the X-ray generating part 1, an X-ray detecting part 2 which detects the X-ray passed through the patient 150, a C-arm 5 which supports the X-ray generating part 1 and the X-ray detecting part 2, and a mechanical control part 3 which controls rotation of the C-arm 5 and movement of a bed plate 17 which the patient 150 is put on.

Moreover, the X-ray imaging apparatus 100 includes an image process memory part 7 which stores X-ray image data and performs several image processes to the X-ray image data, a display part 8 which displays the X-ray image data stored in the image process memory part 7, an operation part 9 by which an operator inputs patient information and several instructions or sets an imaging condition, a distance detection part 6 which detects the distance between the patient 150 and the X-ray generating part 1, and a system controller 10 which controls each part.

The X-ray generating part 1 includes an X-ray tube 15 irradiated to the patient 150, and an X-ray limiting device 16 which forms a cone-shaped X-ray from the X-ray generated by the X-ray tube 15. The X-ray tube 15 is a vacuum tube which generates the X-ray. The X-ray is generated when an electron emitted from a filament is accelerated and collision between the accelerated electron and a tungsten anode occurs. The X-ray limiting device 16 is positioned between the X-ray tube 15 and the patient 150, and limits the X-ray irradiated from the X-ray tube 15 to a size of a predetermined field of view.

The X-ray detecting part 2 includes a flat panel detector 21 where the X-ray passed through the patient 150 is transferred to an electric charge and the electric charge is accumulated, a gate driver 22 which reads out the accumulated electric charge as an X-ray signal, a projection data creating part 13 which creates X-ray projection data based on the electric charge, and a sensor part 26 which measures the distance between the patient 150 and the X-ray detecting part 2. As the flat panel detector 21, a direct conversion type X-ray detector which directly converts the X-ray into the electric charge, or an indirect conversion type X-ray detector which converts the X-ray into the optical signal and then converts the optical signal into the electric charge, may be applied. In this embodiment, the direct conversion type X-ray detector is explained, however the indirect conversion type X-ray detector may be used.

Figure 2:
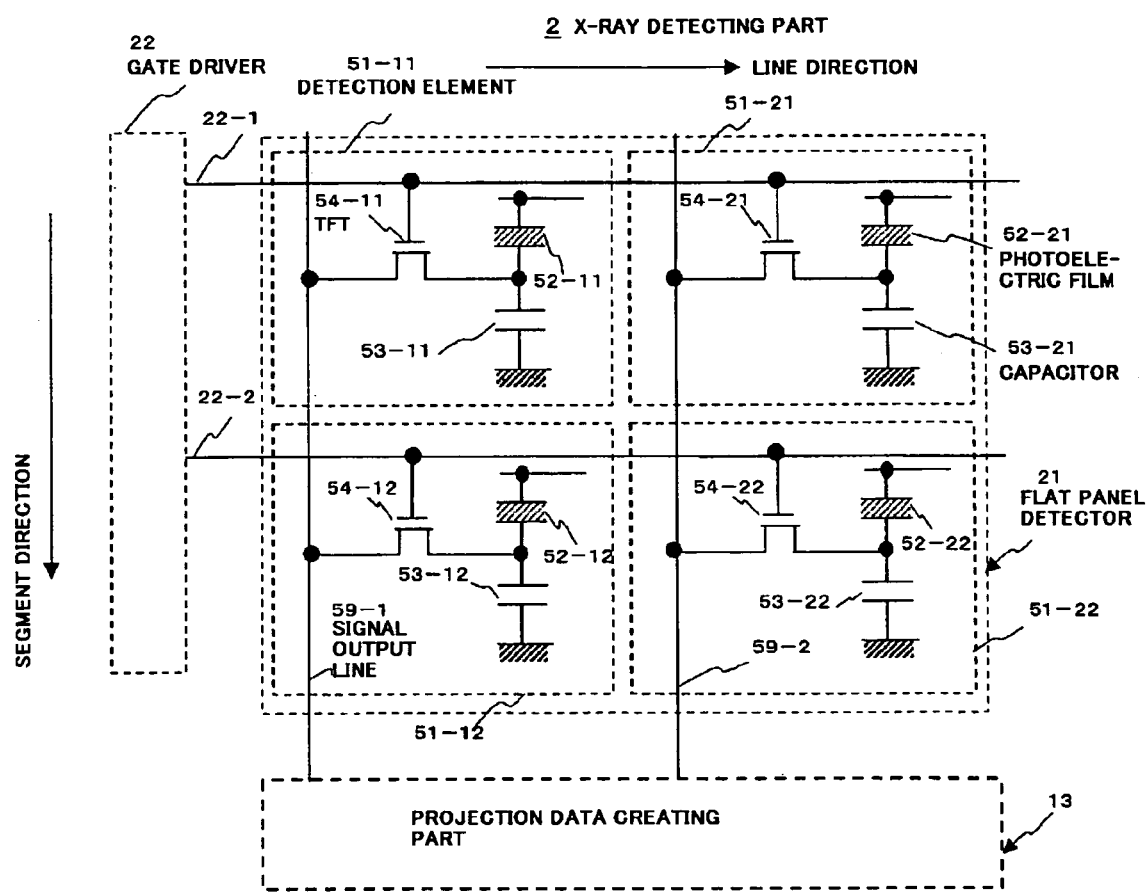
FIG. 2 is a block diagram of a flat panel detector according to the embodiment.

As shown in FIG. 2, the flat panel detector 21 includes a plurality of detection elements 51 which are arranged in two dimensions in a segment direction and a line direction. Each detection element 51 includes a photoelectric film 52 which generates the electric charge according to the incident X-ray, a charge accumulating capacitor 53 which accumulates the electric charge generated in the photoelectric film 52, and a TFT (Thin Film Transistor) 54 which reads out the accumulated electric charge by a predetermined period. To simplify an explanation, it is explained that the flat panel detector includes 2×2 detection elements in the segment direction (up and down direction in FIG. 2) and the line direction (right and left direction in FIG. 2).

First terminals of photoelectric films 52-11, 52-12, 52-21 and 52-22 in FIG. 2 are connected to first terminals of the capacitors 53-11, 53-12, 53-21 and 53-22. Connection points between the first terminals of the photoelectric films and the first terminals of the capacitors are connected to source terminals of the TFT 54-11, 54-12, 54-21 and 54-22. Second terminals of the photoelectric films 52-11, 52-12, 52-21 and 52-22 are connected to a bias power supply. Second terminals of the capacitors 53-11, 53-12, 53-21 and 53-22 are grounded. Gate terminals of the TFT 54-11 TFT 54-21 arranged in the line direction are commonly connected to an output terminal 22-1 of the gate driver 22, and gate terminals of the TFT 54-12 TFT 54-22 are commonly connected to an output terminal 22-2 of the gate driver 22.

Moreover, drain terminals of the TFT 54-11 and 54-12 arranged in the segment direction are commonly connected to a signal output line 59-1, and drain terminals of the TFT 54-21 and 54-22 are commonly connected to a signal output line 59-2. The signal output lines 59-1 and 59-2 are connected to the projection data creating part 13.

In order to read the signal electric charge which is generated in the photoelectric film 52 of the detection element 51 by X-ray irradiation and which is accumulated in the capacitor 53, the gate driver 22 supplies a driving pulse to the gate terminal of the TFT 54.

In FIG. 1, the projection data creating part 13 includes an electric charge/voltage converter 23 which converts the electric charge read from the flat panel detector 21 into voltage, an A/D converter 24 which changes the output of the electric charge/voltage converter 23 into a digital signal, and a parallel serial converter 25 which changes the X-ray projection data which is read in parallel by each line into a time series signal. The sensor part 26 of the X-ray detecting part 2 is explained in a description about the distance detection part 6 below.

The mechanical control part 3 includes a bed plate moving mechanism 32 which moves the bed plate 17 where the patient 150 is placed on in a body axis direction (direction perpendicular to FIG. 1) and in the right and left directions an imaging part moving mechanism 31 which rotates the C arm 5 having the X-ray generating part 1 and the X-ray detecting part 2 around the patient 150 and which moves the X-ray detecting part 2 to the patient 150, and a mechanism controller 33 which controls the rotation and the movement.

Figure 3:
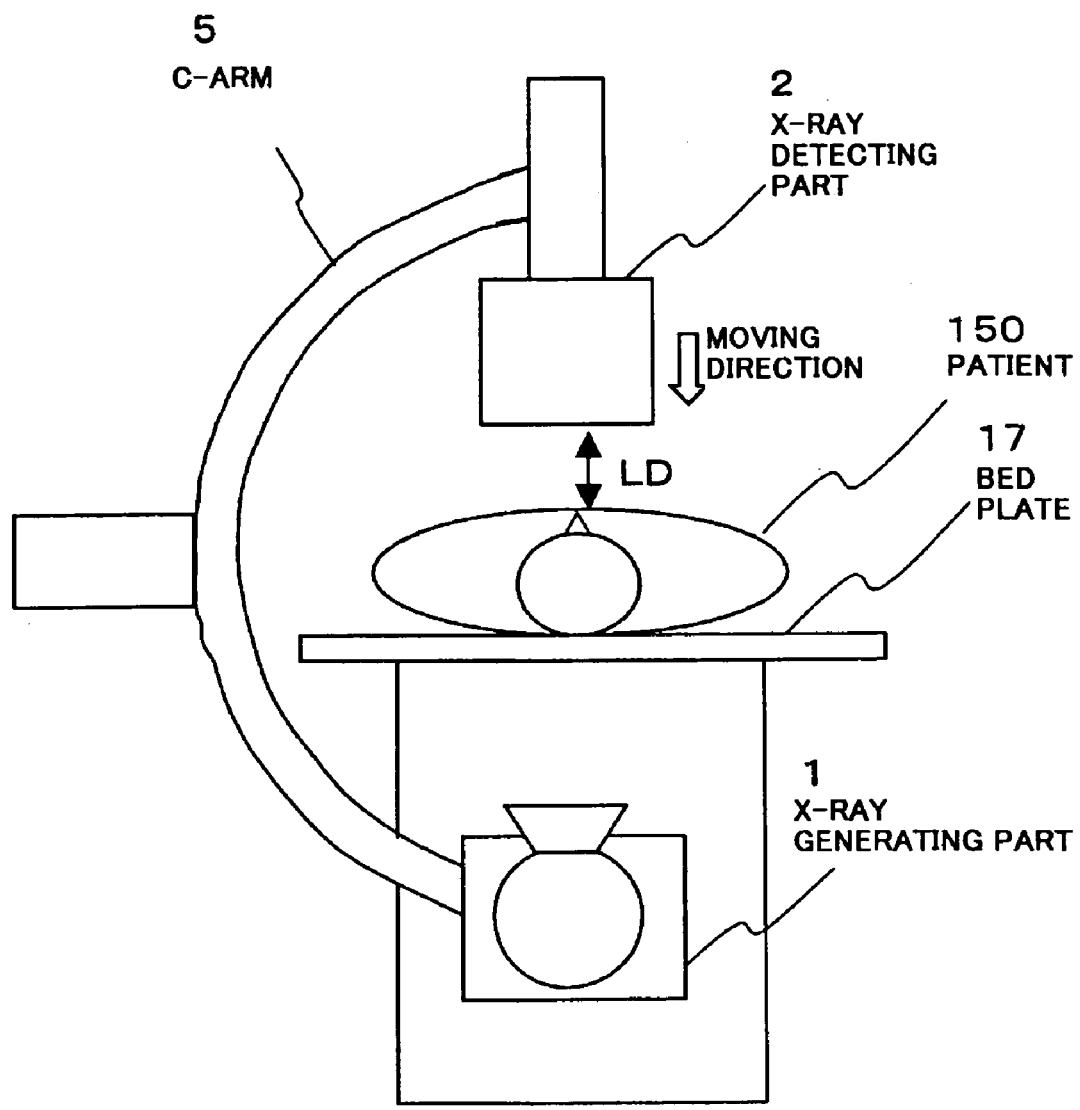
FIGS. 3 is an illustration for explaining movement direction of the flat panel detector according to the embodiment.

According to a control signal supplied from the systems controller 10, the mechanism controller 33 controls the imaging part moving mechanism 31 to set up a direction, amount and speed of the rotation of the C arm 5, or a direction, amount and speed of the rotation/movement of the X-ray detecting part 2. In FIG. 3, the X-ray detecting part 2 and the X-ray generating part 1 which are set up to the patient 150 are shown. The mechanism controller 33 drives the imaging part moving mechanism 31 to move the X-ray detecting part 2, and a desired distance LD between the flat panel detector 21 which is attached in front of the X-ray detecting part 2 and the body surface of the patient 150 is set.

The high-voltage generating part 4 includes a high-voltage generator 42 which generates the high voltage between the filament and the anode to accelerate the electron generated in the filament of the X-ray tube 15, and a high-voltage controller 41 which sets up an X-ray irradiation condition, such as tube current, a tube voltage and an irradiation time, according to an instruction signal from the systems controller 10.

The sensor part 26 of the X-ray detecting part 2 and the distance detection part 6 is explained with reference to FIG. 4.

Figure 7A:
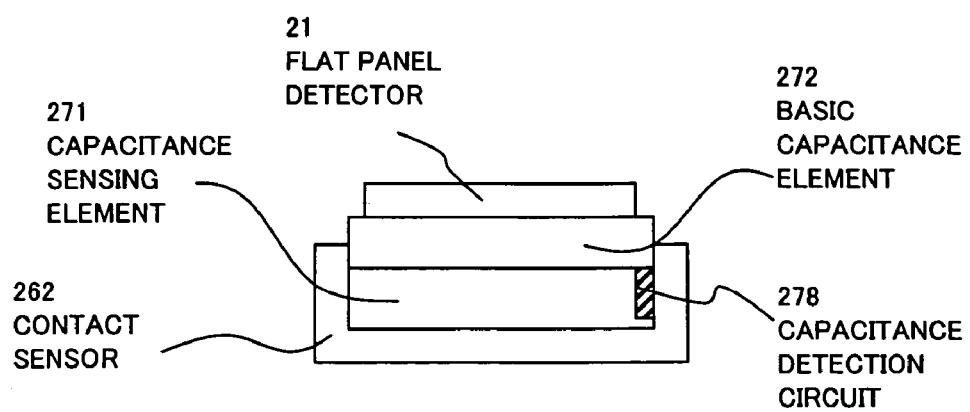
FIGS. 7A and 7B are a cross sectional view and a perspective view of a capacitance sensor according to the embodiment.
Figure 7B:
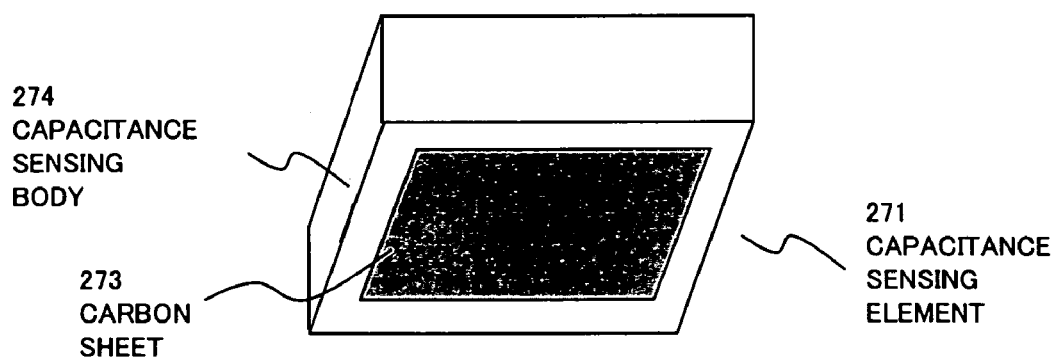

The sensor part 26 is positioned near the flat panel detector 21 in the X-ray detecting part 2 of FIG. 1. The sensor part 26 includes a capacitance sensor 261 which detects the capacitance in front of the flat panel detector 21, a contact sensor 262 which is positioned on a surface of the capacitance sensor 261, and detects the existence of contact for the front of the flat panel detector 21, and a temperature and humidity sensor 263 which measures temperature and humidity near the flat panel detector 21. The capacitance sensor 261 includes a sheet type electrode, such as a carbon sheet, which scarcely prevent the X-ray from passing through. The front of the flat panel detector 21 is covered with the capacitance sensor 261. The contact sensor 262 includes pressure-resistance converting device, for example. The capacitance sensor 261 includes a capacitance sensing element 271 and a basic capacitance element 272 shown in FIG. 7A. The basic capacitance element 272 is grounded. As shown in FIG. 7B, the capacitance sensing element 271 includes a capacitance sensing body 274, the carbon sheet 273 and a capacitance detection circuit 278. The carbon sheet 273 is the substantial same size as the X-ray detection plane. The capacitance sensing body 274 is coated with the carbon sheet. By detecting a capacitance between the carbon sheet 273 and the basic capacitance element 272, the distance to the patient is measured. The carbon sheet may not be the same size as the X-ray detection plane, and may be positioned on a part of the X-ray detection plane.

The distance detection part 6 includes a waveform detection part 60 which supplies a rectangular pulse to the capacitance sensor 261 and measures distortion (delay) of the waveform. The distortion is caused according to the capacitance of the flat panel detector 21. The distance detection part 6 further includes a contact detection circuit 66 which detects whether the flat panel detector 21 contacts the body surface of the patient 150, based on an output signal of the contact sensor 262. The distance detection part 6 further includes a CPU 67 and a memory circuit 68.

The waveform detection part 60 includes a rectangle wave generator 61 which generates the rectangular pulse by a predetermined period, and a driving circuit 62 which amplifies and supplies the rectangular pulse to the capacitance sensor 261. The waveform detection part 60 further includes a preamplifier 63 which amplifies and reform the rectangular pulse where the waveform distortion occurs according to the capacitance of the capacitance sensor 261, and a phase discriminator 64 which detects a direct-current component by performing a phase detection between an output of the rectangle wave generator 61 and an output of the preamplifier 63.

Figure 5A:
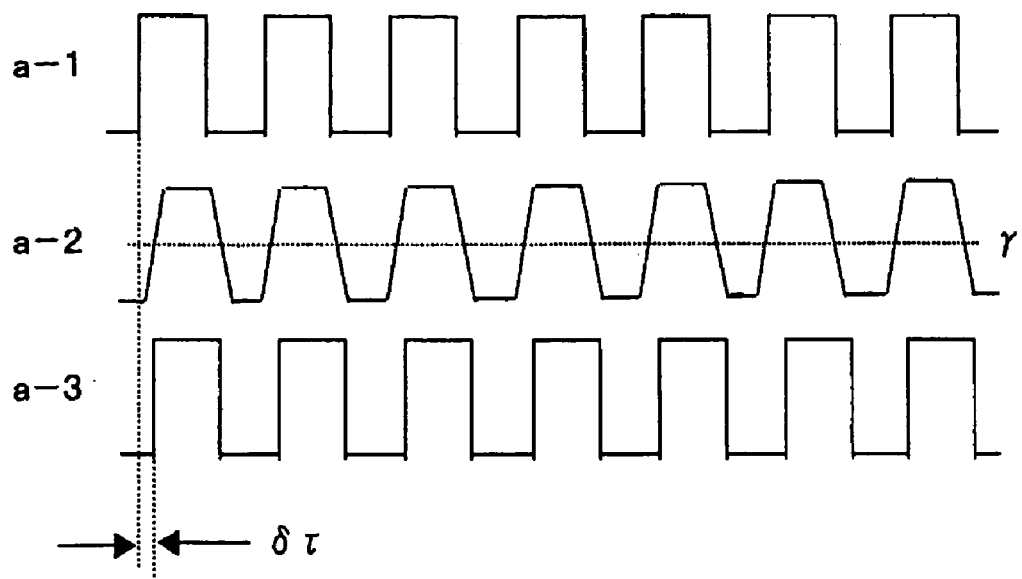
FIGS. 5A and 5B are graphs for explaining a measurement method of a value of capacitance according to the embodiment.
Figure 5B:
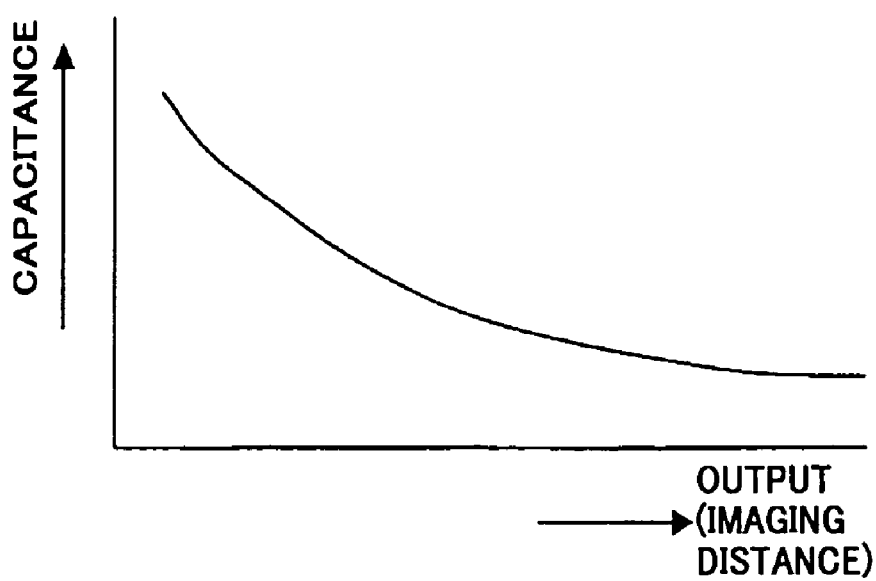

An operation of method for measuring the capacitance in the waveform detection part 60 is explained with reference to FIGS. 5A and 5B. A waveform a-1 in FIG. 5A is a rectangular waveform which is outputted from the rectangle wave generator 61 of the waveform detection part 60, and a waveform a-2 is a rectangular waveform which is an input to the preamplifier 63 and which is affected by the waveform distortion. A waveform a-3 is an output of the preamplifier 63, the output of which is reformed using a threshold γ to the waveform a-2. In this case, when the waveform a-1 is impressed to the capacitance sensor 261 via the driving circuit 62, the waveform distortion occurs in the waveform a-1, namely the waveform a-2, according to the capacitance. A waveform a-3 is a reformed pulse of the waveform a-2 and is delayed by a phase difference δt from the waveform a-1 according to the capacitance.

DC output of the phase discriminator 64 which the waveform a-1 and a-3 are inputted shows a low value when the distortion is large or the capacitance is large. Therefore, as shown in FIG. 5B, the capacitance of the flat panel detector 21 is presumed by measuring a size of the output signal of the phase discriminator 64, and also it is possible to presume the distance (referred to as imaging distance below) between the flat panel detector 21 and the body surface of the patient by obtaining the value of the capacitance while the X-ray detecting part 2 moves.

However, patient characteristics, such as a patient's shape, age, sex and degree of obesity, affect the capacitance, and an error caused by a change of the capacitance can occur to the imaging distance to be presumed. Similarly the capacitance changes according to environment around the X-ray detecting part 2 and the patient 150. Especially an error resulting from humidity can be important.

The patient characteristics and the environment, such as the humidity or temperature, may be corrected.

Figure 4:
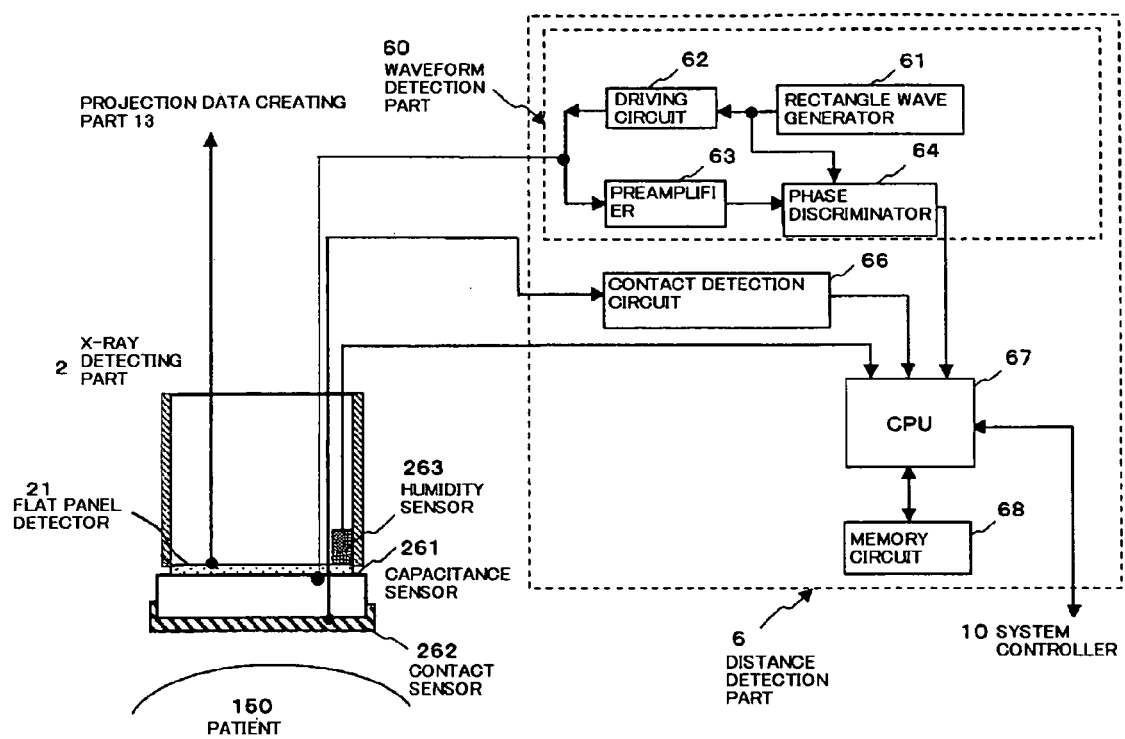
FIG. 4 is a block diagram of a sensor and a distance detection part.

The memory circuit 68 in the distance detection part 6 in FIG. 4 has a capacitance-imaging distance memory area where a relationship between an imaging distance which is set to a general patient and the capacitance which is presumed based on the output signal from the waveform detection part 60 is stored. The memory circuit 68 further has a patient information memory area where the patient information, such as a diagnosis part, age, sex and degree of obesity of the patient 150 is stored, and an environment information memory area where the environment information, such as the humidity or the temperature, around the flat panel detector 21 is stored. The memory circuit 68 further includes a correction coefficient memory area where a correction coefficient of the capacitance to the patient information or the environment information.

Furthermore, the memory circuit 68 includes a detection output-capacitance data memory area where a relationship between the detection output from the waveform detection part 60 shown in FIG. 4 and the capacitance of the capacitance sensor 261 is stored in advance.

The general data of the above mentioned relationship between the imaging distance and the capacitance and the correction coefficient of the capacitance to the patient information and the environment information can be obtained based on a plurality of sets of data which are accumulated in past X-ray imaging, or a phantom can be used instead. Data of the relationship between the output of the phase discriminator 64 and the capacitance can be obtained by performing a basic experimentation in advance.

The CPU 67 receives the output of the contact detection circuit 66 and the measured temperature value and the humidity value from the temperature and humidity sensor 263 in addition to the output signal from the phase discriminator 64 in the waveform detection part 60. When the output signal of the phase discriminator 64 is received, the capacitance is calculated based on this output signal and the relationship data between the detection output and the capacitance stored in the detection output-capacitance data memory area. Furthermore, the capacitance is corrected to obtain corrected capacitance (referred to as corrected capacitance) is calculated by the correction coefficient selected from a plurality of correction coefficients stored in correction coefficient memory area based on the patient information data and the environment information stored in the patient information memory area and the environment information memory area.

The CPU 67 calculates the imaging distance based on the relationship data stored in the capacitance-imaging distance memory area. When the calculated imaging distance is a first value $\alpha$ or a second value $\beta$, the CPU 67 supplies an approach signal to the system controller 10.

In FIG. 1, the image process memory part 7 has a function to generate the X-ray image data to be displayed in the display part 8. The image process memory part 7 includes an image-processing circuit 71 for performing image processing to the X-ray projection data outputted from the projection data creating part 13. The image process memory part 7 further includes an image data memory circuit 72 for memorizing the above-mentioned X-ray projection data and the X-ray image data after image processing. The image-processing circuit 71 performs an image processing for generating DSA image data based on subtraction between contrast image data and mask image data which are obtained before and after contrast agent is injected, long image data and 3D image data, for example.

The operation part 9 is an input device, such as a keyboard, a trackball, a joystick, a mouse, or a display panel or an interactive interface having various switches, etc, for example. The operation part 9 is used for inputting the patient information, for setting the first value $\alpha$ indicating a deceleration point of the moving speed of the X-ray detecting part 2 and the second value $\beta$ indicating a stop point of the X-ray detecting part 2, for inputting a start instruction of the imaging, and for setting an appropriate X-ray imaging condition for the diagnosis part. The imaging condition includes a tube voltage, a tube current impressed to the X-ray tube 15, and a irradiation time of the X-ray, etc. The patient information includes age, sex, height, weight, degree of obesity, inspection part, past diagnostic history, etc.

When a Patient ID is inputted from the operation part 9, the patient information or the various imaging condition based on the patient information are automatically read from HIS (hospital information system) which is connected through the network, and an operator adjusts the information and the imaging condition, if necessary.

The display part 8 is used for displaying the image data stored in the image data memory circuit 72 of the image process memory part 7. The display part 8 includes a data generation circuit 81 which creates the image data to be displayed, combining the image data and attached information, such as number or a letter. The display part 8 further includes a conversion circuit 82 which creates a display signal, performing D/A conversion and TV format conversion to the image data or the attached information, and a monitor 83, such as a liquid crystal monitor or CRT monitor, which displays the display signal.

Figure 6:
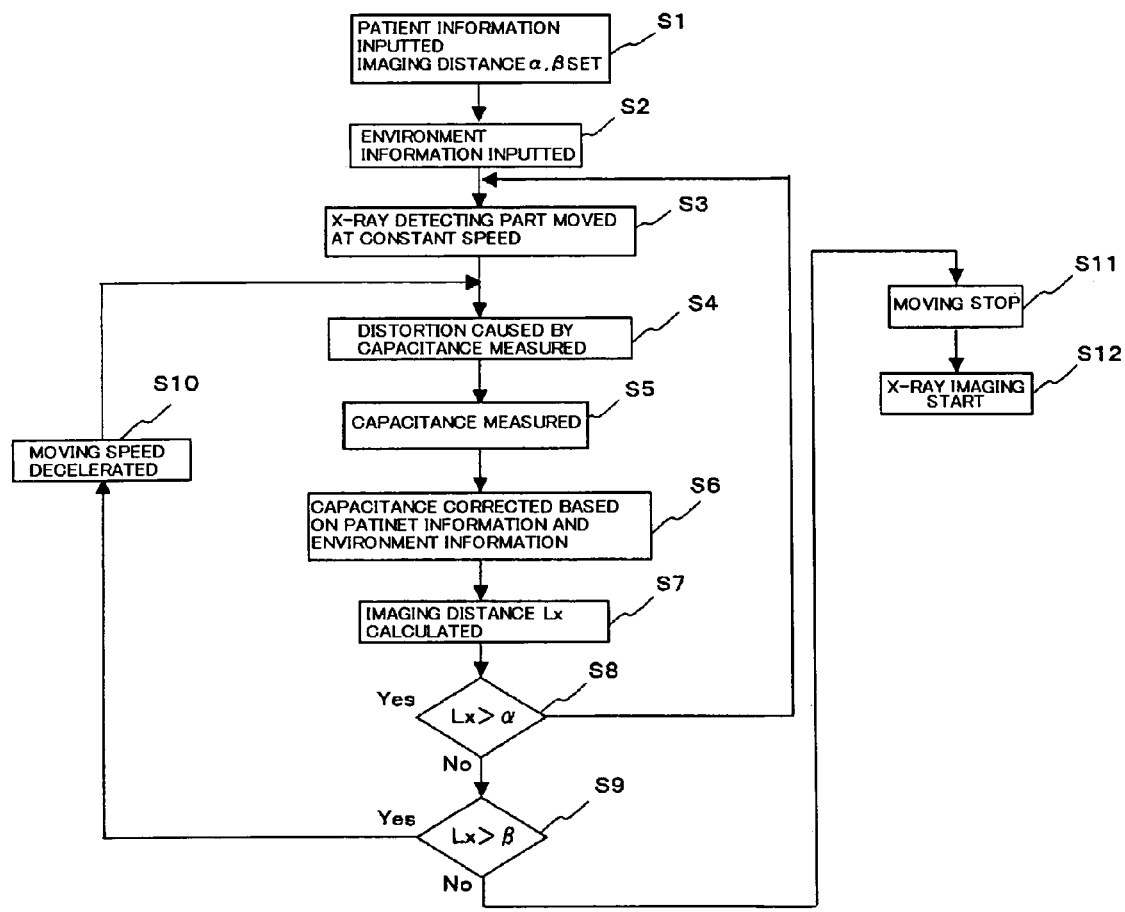
FIG. 6 is a flow chart for explaining an operation of position setting of the flat panel detector according to the embodiment.

A position setting procedure of the imaging part in the X-ray imaging apparatus 100 is explained with reference to FIG. 1 through 6. FIG. 6 is a flow chart which shows the setting procedure of the imaging part.

When a power of X-ray imaging apparatus 100 is switched to ON, the X-ray imaging apparatus 100 starts to be connected to a server or HIS which is located in the same medical facilities through the network. Subsequently, when the operator inputs the patient ID of the patient 150 with the operation part 9, a CPU in the system controller 10 reads out the patient information and the imaging condition which correspond to the patient ID from the server or the HIS. The patient information and the imaging condition are memorized in a memory circuit in the system controller 10 and are displayed in a display panel of the operation part 9.

The operator checks the above-mentioned information displayed on the display panel of the operation part 9 and adjusts them if needed. The operator selects the patient's 150 diagnosis part, age, sex, degree of obesity, etc. using an input device from the patient information. The selected information is stored in the patient information memory area in the memory circuit 68 of the distance detection part 6.

The operator sets up a moving condition of the imaging part among the various imaging conditions displayed on the display panel of the operation part 9. For example, the deceleration point value $\alpha$ and the stop point value $\beta$ ($\beta>\alpha$) of the imaging part are set and stored in the memory circuit 68 via the CPU 67 of the distance detection part 6 (Step S1 of FIG. 6).

Subsequently, the CPU 67 of the distance detection part 6 receives the temperature value and humidity value which are obtained from the temperature and humidity sensor 263 positioned inside of the X-ray detecting part 2, and these values are saved in the environment information memory area of the memory circuit 68 (Step S2 of FIG. 6).

After the patient information and the environment information are stored, the systems controller 10 supplies a command signal for rotating/moving the imaging part to the mechanism controller 33. The mechanism controller 33 which received the command signal supplies a control signal to the imaging part moving mechanism 31 to rotate the C-arm to a desired angle in a desired direction at a desired speed. Similarly, when an imaging direction is set, the mechanism controller 33 supplies a control signal to the imaging part moving mechanism 31, and the X-ray detecting part 2 moves close to or far from the patient 150 at a desired speed (Step S3 of FIG. 6).

Next, the rectangle-wave generator 61 of the waveform detection part 60 supplies the rectangular pulse to the capacitance sensor 261 in a predetermined cycle through the driving circuit 62 while the X-ray detecting part 2 moves. At this time, the waveform distortion occurs to the rectangular pulse supplied to the capacitance sensor 261 having a capacitance. The rectangular pulse with the waveform distortion is amplified and reformed in the preamplifier 64 of the waveform detection part 60, and is inputted into the first input terminal of the phase discriminator 63. The rectangular pulse outputted from the rectangle wave generator 61 is inputted into the second input terminal of the phase discriminator 64. In the phase discriminator 64, the rectangular pulse outputted from the rectangle wave generator 61 and the output of the preamplifier 63 are discriminated by phase, and are inputted into the CPU 67 (Step S4 of FIG. 6).

The CPU 67 calculates the capacitance corresponding to the size of the output (direct-current component) of the phase discriminator 64 based on the relationship data of the detection output and the capacitance stored in the detection output-capacitance data memory area of the memory circuit 68 (Step S5 of FIG. 6).

The CPU 67 reads out the temperature information and humidity information stored in the environment information memory area of the memory circuit 68, and the patient information, such as diagnosis part, body information (height, weight degree of obesity), age and sex stored in the patient information memory area of the memory circuit 68. The correction coefficient is selected from the correction coefficient information memory area based on the patient information and the environment information. The capacitance obtained in Step S5 is corrected using the correction coefficient to obtain the corrected capacitance (Step S6 of FIG. 6).

The CPU 67 calculates the imaging distance Lx according to the corrected capacitance in Step S6 using the relationship information of the capacitance and the imaging distance stored in the capacitance-imaging distance memory area of the memory circuit 68 (Step S7 in FIG. 6).

When the obtained imaging distance Lx is bigger than the imaging distance of the first value α (Step S8 in FIG. 6), the X-ray detecting part 2 moves at a constant speed to the patient 150, and Step S3 through S7 are repeated. When the imaging distance Lx is not more than the deceleration imaging distance of the first value α, the imaging distance Lx is compared with the stop imaging distance of the second value β (Step S9 in FIG. 6)

When the imaging distance Lx is bigger than the stop imaging distance of the second value β, the CPU 67 supplies a first approach signal to the systems controller 10, and the mechanism controller 33 which received a command signal from the systems controller 10 based on the first approach signal controls the imaging part moving mechanism 31 and decelerates the speed of the X-ray detecting part 2 (Step S10 of FIG. 6). Step S4 and S10 are repeated.

When the imaging distance Lx is not more than the stop imaging distance of the second value β, the CPU 67 supplies the second approach signal to the systems controller 10, and the mechanism controller 33 which received a command signal from the systems controller 10 based on the second approach signal supplies a stop signal to the imaging part moving mechanism 31, and the movement of the X-ray detecting part 2 stops (Step S11 of FIG. 6).

As stated above, when the X-ray detecting part 2 which moves at the constant speed towards a the patient 150 reaches the deceleration imaging distance, it starts to decelerate, and when the imaging distance reaches to the stop imaging distance, the X-ray detecting part 2 stops.

When the X-ray detecting part 2 is set as the desired imaging distance of the second value β, the operator inputs the start command of the X-ray imaging with the operation part 9. The X-ray imaging starts by supplying the start command to the systems controller 10 (Step S12 of FIG. 6).

The high voltage controller 41 of the high voltage generating part 4 receives the start command from the systems controller 10, controls the high voltage generator 42 based on the already set-up X-ray irradiation condition, impresses the high voltage to the X-ray tube 15 of the X-ray generating part 1, and irradiates the X-ray to the patient 150 through the X-ray limiting device 16. The X-ray which passes through the patient 150 is detected by the flat panel detector 21 of the X-ray detecting part 2 positioned behind the patient 150.

The flat panel detector 21 including the X-ray detection elements 51 which are arranged in the line direction and the segment direction as shown in FIG. 2. The X-ray detection elements 51 receives the X-ray which passes the patient 150, and the signal electric charge corresponding to intensity of the X-ray irradiation is accumulated in the charge accumulating capacitor 53 of the X-ray detection element 51. After the X-ray irradiation is completed, the gate driver 22 to which a clock pulse is supplied from the systems controller 10 reads the signal electric charge accumulated in the charge accumulating capacitor 53 of the X-ray detection element 51 by supplying the driving pulse to the flat panel detector 21.

The read out signal electric charge is converted into the voltage signal in the electric charge/voltage converter 23 in the projection data creating part 13 shown in FIG. 1. The voltage signal is changed into a digital signal in the A/D converter 24, and is temporally memorized as projection data in a memory circuit of the parallel serial converter 25. The systems controller 10 reads the projection data in order serially per line, and stores the projection data as 2-dimensional projection data in the projection data memory are of the image data memory circuit 72 of the image process memory part 7.

The image-processing circuit 71 of the image process memory part 7 reads the 2-dimensional projection data stored in the image data memory circuit 72, creates the image data by performing image processing, such as outline emphasis and gradation change, if needed, and stores the created image data in the image data memory are of the image data memory circuit 72.

The systems controller 10 reads the image data stored in the image data memory circuit 72, and displays the image data on the monitor 83 of the display part 8. In detail, the systems controller 10 reads the image data stored in the image data memory circuit 72, and in the data generation circuit 81 for a display of the display part 8, the attached information, such as number or a letter, is combined to the image data, and the combined data is supplied to a conversion circuit 82. In the conversion circuit 82, the D/A conversion and the TV format conversion are performed on the combined data, and the converted data is displayed on the monitor 83.

According to the above embodiment, since the front of the flat panel detector 21 is covered with the capacitance sensor, the imaging distance to the closest part of the patient can be set according to the shape of the patient surface.

Moreover, when the capacitance is corrected according to not only the shape of the patient's diagnosis part but also the patient information, the patient's shape, age, sex, degree of obesity, etc, the imaging distance can be appropriately set. Furthermore, when the correction of the capacitance is performed based on a database created in advance, the capacitance can be corrected stably and simply.

Therefore, the X-ray detecting part can be moved to a desired position to the patient without contact, and it is possible to obtain clear image data efficiently.

Figure 8A:
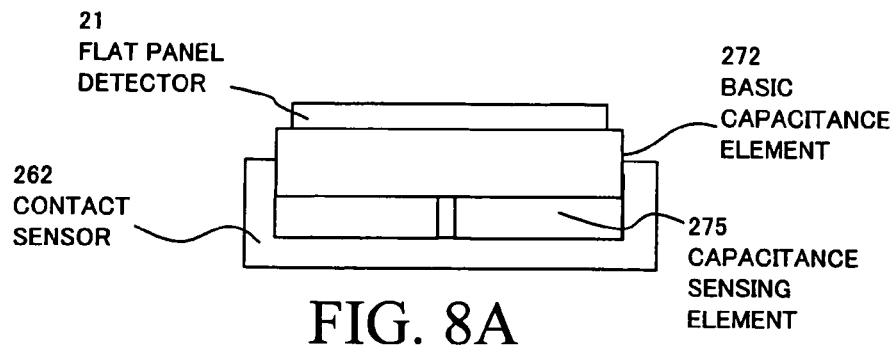
FIG. 8A through 8C are a cross sectional view, a perspective view and a top view of the capacitance sensor.
Figure 8B:
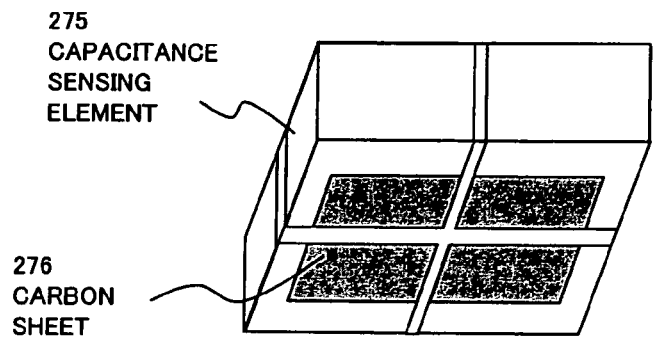
Figure 8C:
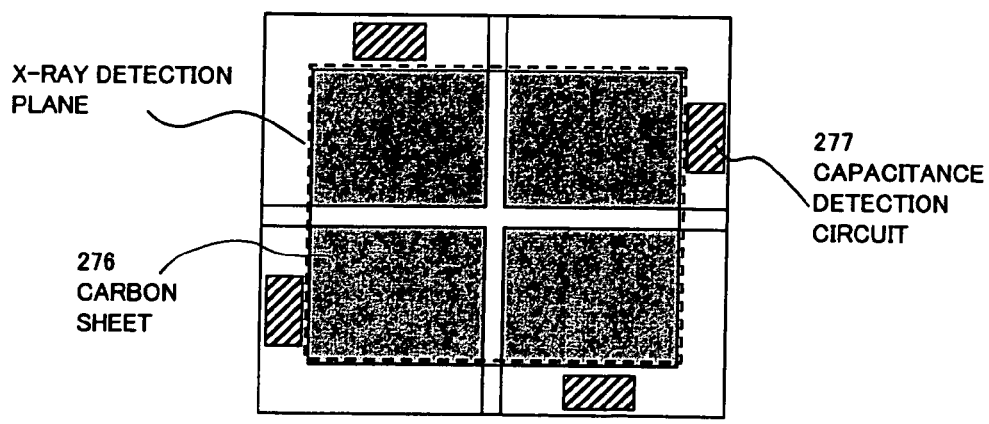

A modification of the capacitance sensor is explained with reference to FIG. 8A through 8C. In the modification, as shown in FIG. 8B, a capacitance sensing element 275 is divided into four elements. As well as the capacitance sensing element 275, a carbon sheet 276 is also divided into four sheets. The capacitance between each carbon sheet 276 and the basic capacitance element 272 is obtained by each capacitance detection circuit 277, and the imaging distance is measured. Two lines of the division of the capacitance sensing elements are positioned along the arrangement of the X-ray detection elements in the line direction and the segment direction. The carbon sheet may be positioned such that at least part of the carbon sheet overlaps the X-ray detection plane (indicated as a broken line) of the flat panel detector. In the modification, since a plurality of the capacitance sensing elements are adapted, it is possible to measure the imaging distance appropriately.

The embodiment and the modification are mentioned above, however the embodiment and the modification may be modified For instance, in the embodiment, the case where the X-ray detecting part moves to the patient is explained, the embodiment ant the modification may be applied to a case where the X-ray generating part may be move to the patient. As another example, when a plurality of the capacitance sensing elements are used, the line of the division may not be positioned along the arrangement of the X-ray detection elements. As another example, the basic capacitance element may be adjusted instead of grounded.

Moreover, although the case where the value of the capacitance is obtained using the sheet type electrode of the capacitance sensor and the capacitance is corrected according to the patient information is explained, at least one of technique of the sheet type electrode of the capacitance sensor and technique of the correction according to the patient information may be used. Moreover, the patient information may not be limited to the patient's shape, age, sex and degree of obesity.

Although the flat panel detector is explained for detecting the X-ray, an I.I and an X-ray TV may be used instead. Although the phase discriminating method for measuring the influence of the capacitance is explained, other method may be used. Although the angio X-ray imaging apparatus including the C-arm is mainly explained, other X-ray imaging apparatus, such as RF X-ray imaging apparatus, may be used.

Although two type of the imaging distances of the deceleration point α and the stop point β are explained, only stop point β may be used.

What is claimed is:

1. An X-ray imaging apparatus, comprising:
   an X-ray irradiating unit configured to irradiate an X-ray to an object;
   an X-ray detecting unit configured to detect the irradiated X-ray;
   an image creating unit configured to create X-ray image data based on data detected by the X-ray detecting unit;
   a moving mechanism configured to move the X-ray detecting unit to the object;
   a capacitance sensing unit, including an electrode which is positioned so as to cover at least part of a detection plane of the X-ray detecting unit, configured to obtain a capacitance value of the X-ray detecting unit by the electrode;
   an adjustment unit configured to correct the capacitance value based on a selection of a correction coefficient from a plurality of correction coefficients related to object information; and
   a distance measurement unit configured to measure a distance between the object and the X-ray detecting unit based on the corrected capacitance value.

2. The X-ray imaging apparatus according to claim 1, wherein the electrode covers a whole area of the detection plane of the X-ray detecting unit.

3. The X-ray imaging apparatus according to claim 1, wherein the electrode is a carbon sheet.

4. The X-ray imaging apparatus according to claim 3, wherein the X-ray detecting unit including a flat panel detector where a plurality of X-ray detection elements are arranged two dimensionally.

5. The X-ray imaging apparatus according to claim 4, wherein the electrode is divided into quadrants aligned with an X-ray detection plane of the X-ray detection elements.

6. The X-ray imaging apparatus according to claim 1, wherein the electrode is divided to a plurality of electrodes, and the capacitance sensing unit obtains capacitance values of the plurality of electrodes.

7. The X-ray imaging apparatus according to claim 6, wherein the electrode is divided to four electrodes.

8. The X-ray imaging apparatus according to claim 1, wherein the corrected capacitance is additionally based on environmental data regarding a temperature and a humidity around the object.

9. The X-ray imaging apparatus according to claim 1, wherein the moving mechanism stops the X-ray detecting unit based on the measured distance before the X-ray detecting unit contacts the object.

10. The X-ray imaging apparatus according to claim 1, wherein the moving mechanism changes a moving speed of the X-ray detecting unit based on the measured distance.

11. An X-ray imaging apparatus, comprising:
    an X-ray irradiating unit configured to irradiate an X-ray to an object;
    an X-ray detecting unit configured to detect the irradiated X-ray;
    an image creating unit configured to create X-ray image data based on data detected by the X-ray detecting unit;
    a moving mechanism configured to move the X-ray detecting unit to the object;
    a capacitance sensing unit including an electrode and configured to obtain a capacitance value of the X-ray detecting unit by the electrode;

an environment sensing unit configured to obtain environment information around the object;
a capacitance correction unit configured to correct the capacitance value based on the environment information and based on a selection of a correction coefficient from a plurality of correction coefficients related to object information; and
a distance measurement unit configured to measure a distance between the object and the X-ray detecting unit based on the corrected capacitance value.

12. An X-ray imaging apparatus, comprising:
an X-ray irradiating unit configured to irradiate an X-ray to an object;
an X-ray detecting unit configured to detect the irradiated X-ray;
an image creating unit configured to create X-ray image data based on data detected by the X-ray detecting unit;
a moving mechanism configured to move the X-ray detecting unit to the object;
a capacitance sensing unit including an electrode and configured to obtain a capacitance value of the X-ray detecting unit by the electrode;
an input device configured to input information of the object;
a capacitance correction unit configured to correct the capacitance value based on the object information and based on a selection of a correction coefficient from a plurality of correction coefficients related to object information; and
a distance measurement unit configured to measure a distance between the object and the X-ray detecting unit based on the corrected capacitance value.

13. An X-ray imaging apparatus, comprising:
an X-ray irradiating unit configured to irradiate an X-ray to an object;
an X-ray detecting unit configured to detect the irradiated X-ray;
an image creating unit configured to create X-ray image data based on data detected by the X-ray detecting unit;
a moving mechanism configured to move the X-ray detecting unit to the object;
a capacitance sensing unit including an electrode and configured to obtain a capacitance value of the X-ray detecting unit by the electrode;
an input device configured to input information of the object;
a capacitance correction unit configured to correct the capacitance value based on the object information; and
a distance measurement unit configured to measure a distance between the object and the X-ray detecting unit based on the corrected capacitance value
wherein the object information includes at least one of shape, age, sex and degree of obesity of the object.

14. An X-ray imaging apparatus, comprising:
an X-ray irradiating unit configured to irradiate an X-ray to an object;
an X-ray detecting unit configured to detect the irradiated X-ray;
an image creating unit configured to create X-ray image data based on data detected by the X-ray detecting unit;
a moving mechanism configured to move the X-ray detecting unit to the object;
a capacitance sensing unit including an electrode and configured to measure a capacitance value between the electrode and the object;
an input device configured to input information of the object;
a capacitance correction unit configured to correct the measured capacitance value based on the object information; and
a distance measurement unit configured to measure a distance between the object and the X-ray detecting unit based on the corrected capacitance value.

15. A method for moving an X-ray detector, comprising:
irradiating an X-ray to an object by an X-ray irradiating unit;
detecting the irradiated X-ray by an X-ray detecting unit;
creating X-ray image data based on data detected in the detecting;
moving the X-ray detecting unit to the object;
obtaining a capacitance value of the X-ray detecting unit by an electrode which is positioned so as to cover at least part of a detection plane of the X-ray detecting unit;
correcting the capacitance value based on a selection of a correction coefficient from a plurality of correction coefficients related to object information; and
measuring a distance between the object and the X-ray detecting unit based on the corrected capacitance value.

16. A method for moving an X-ray detector, comprising:
irradiating an X-ray to an object by an X-ray irradiating unit;
detecting the irradiated X-ray by an X-ray detecting unit;
creating X-ray image data based on data detected by the X-ray detecting unit;
moving the X-ray detecting unit to the object;
obtaining a capacitance value of the X-ray detecting unit;
obtaining environment information around the object;
correcting the capacitance value based on the environment information and based on a selection of a correction coefficient from a plurality of correction coefficients related to object information; and
measuring a distance between the object and the X-ray detecting unit based on the corrected capacitance value.

17. A method for moving an X-ray detector, comprising:
irradiating an X-ray to an object by an X-ray irradiating unit;
detecting the irradiated X-ray by an X-ray detecting unit;
creating X-ray image data based on data detected by the X-ray detecting unit;
moving the X-ray detecting unit to the object;
obtaining a capacitance value of the X-ray detecting unit;
inputting information of the object;
correcting the capacitance value based on the object information and based on a selection of a correction coefficient from a plurality of correction coefficients related to object information; and
measuring a distance between the object and the X-ray detecting unit based on the corrected capacitance value.

18. A method for moving an X-ray detector, comprising:
irradiating an X-ray to an object by an X-ray irradiating unit;
detecting the irradiated X-ray by an X-ray detecting unit;
creating X-ray image data based on data detected by the X-ray detecting unit;
moving the X-ray detecting unit to the object;
measuring a capacitance value between an electrode of the X-ray detecting unit and the object;
inputting information of the object;
correcting the capacitance value based on the object information; and
measuring a distance between the object and the X-ray detecting unit based on the corrected capacitance value.

* * * * *